United States Patent [19]

Johnson

[11] Patent Number: 5,088,315
[45] Date of Patent: Feb. 18, 1992

[54] GAS PURITY ANALYZER AND METHOD
[76] Inventor: Walter A. Johnson, W233 S6900, Big Bend, Wis. 53103
[21] Appl. No.: 581,004
[22] Filed: Sep. 12, 1990
[51] Int. Cl.[5] .............................................. G01N 7/00
[52] U.S. Cl. ........................................................ 73/23.2
[58] Field of Search ................... 73/23.2, 31.04, 29.01, 73/29.03, 25.04

[56] References Cited
U.S. PATENT DOCUMENTS

| | | | |
|---|---|---|---|
| 3,312,101 | 4/1967 | Melfi, Jr. et al. | 73/31.04 |
| 3,691,818 | 9/1972 | Emerson | 73/31.04 |
| 4,101,277 | 7/1978 | Hickam | 73/23.2 X |

FOREIGN PATENT DOCUMENTS 2259459  6/1974  Fed. Rep. of Germany ....... 73/23.2

Primary Examiner—Hezron E. Williams
Assistant Examiner—Joseph W. Roskos
Attorney, Agent, or Firm—Andrus, Sceales, Starke & Sawall

[57] ABSTRACT

A method for providing a real time measurement of the purity of one gas in a binary mixture of two known gases, which mixture also contains water vapor, applies principles of the fan laws and ideal gas laws in a manner whereby the volume percent purity of the gas may be calculated directly from measured fan differential pressure. The calculted purity is preferably corrected for variations in temperature and pressure. The method requires the determination and use of an appropriate fan constant based on the gas whose purity is to be measured and specific to the fan being used to circulate the gas mixture and the speed at which it operates. An appropriate adjustment factor for differences between design and measured speed may also be applied in acordance with the fan laws. The method is particularly well adapted to provide real time measurement of hydrogen gas purity in the cooling gas circulated inside a large synchronous AC generator and utilizing a microprocessor to provide a real time output of hydrogen gas purity. The principles underlying the method of the invention are also utilized to develop a correction factor to convert hydrogen purity measured from a dry gas mixture sample using a thermal gas analyzer to a true hydrogen purity. The method may further to applied to calculate actual water vapor content in a sample from which hydrogen purity was measured by a thermal gas analyzer.

15 Claims, 1 Drawing Sheet

GAS PURITY ANALYZER AND METHOD

BACKGROUND OF THE INVENTION

The present invention pertains to the determination of the purity of a gas in a gas mixture and, more particularly, to a method and apparatus for determining the purity of a first gas in a binary mixture with another known gas which mixture is being circulated in a closed system by a fan.

Binary mixtures of two gases are often utilized in various kinds of closed systems, for example, to process certain materials therein or to provide a medium for heat transfer. As an example of the latter, a hydrogen gas with an air impurity fraction is often used to cool large AC generators by circulating the gas mixture within the generator housing. Hydrogen, in particular, has a very high thermal conductivity which makes it possible to run large generators at higher loads because the circulating hydrogen provides better removal of heat from the generator windings. The thermal conductivity of hydrogen is six to seven times greater than air and, therefore, as high a percentage of hydrogen as practical in the cooling gas mixture is most desirable.

Because of the highly combustible nature of hydrogen, the volume percent or purity of hydrogen in the mixture must also be maintained relatively high. It is desirable in this heat transfer application to maintain the purity of hydrogen in the mixture above 90% and, more typically, above a minimum of 95%. Obviously, because of the practical impossibility of obtaining pure hydrogen gas and the presence of normal system leakage, a pure hydrogen atmosphere cannot be maintained. Nevertheless, hydrogen purities as high as 98% to 99% are fairly readily attainable.

It is also necessary, in order to take best advantage of the high thermal conductivity of hydrogen to maintain an adequate pressure within the system. In a large AC generator, for example, operation at full load requires the maintenance of a system pressure up to about 75 psi. Typical hydrogen leakage through the generator shaft seals or by absorption in the lubricating oil requires the regular addition of makeup hydrogen, both to maintain system pressure and to maintain hydrogen purity at a safe high level.

Because of the potential hazards which are attendant a reduction in hydrogen purity below safe, noncombustible levels, appropriate purity monitoring and alarm systems must be utilized. The primary means of monitoring hydrogen purity in the cooling gas mixture inside a large AC generator is by the use of a thermal gas analyzer. Because the relative conductivity of hydrogen is so much greater than the air or other gas impurity with which it is typically mixed, thermal conductivity is an excellent indicator of hydrogen purity. Thus, a thermal gas analyzer is typically used to continuously monitor hydrogen purity and to provide an appropriate alarm if the purity drops below established safe levels. However, typical thermal gas analyzers have a notoriously slow response time and it is not unusual for the output of a thermal gas analyzer to lag an actual system change in hydrogen purity by as much as one hour. Obviously, the alarm signal will also lag correspondingly the actual alarm condition. In addition, a typical thermal gas analyzer requires the use of a dryer in the sample feedline to remove moisture from the gas sample prior to analysis. With water vapor removed from the air/hydrogen sample being analyzed, the sample is not actually representative of the gas mixture used in the generator cooling system An independent back-up means of determining hydrogen purity is typically provided by the use of a direct reading manometer calibrated to give a rough indication of hydrogen purity in the generator. The manometer is calibrated empirically based on measured gas purities at various measured machine pressures. A typical large generator includes two shaft-mounted fans inside the housing to circulate the cooling hydrogen/air mixture. Differential fan pressure is monitored directly with the appropriately calibrated manometer which also provides a much more rapid response to changes in hydrogen purity than does a thermal gas analyzer. However, a manometer provides only a rough indication of hydrogen purity and is typically difficult to read accurately. Moreover, a manometer cannot be readily connected to be read or monitored at a remote location nor can it be easily adapted to be connected to an alarm system.

There is, therefore, a need for a method and apparatus for determining the purity of one gas in a known binary gas mixture which is accurate and operates on an essentially real time basis. In particular, it would be desirable to have a method and means for accurately and rapidly monitoring hydrogen purity in the coolant gas mixture circulating within a large generator or the like. Further, it would be desirable to have a method in which the water vapor fraction in a binary gas mixture could be properly included in determining the actual purity or volume fraction of either of the two gases.

SUMMARY OF THE INVENTION

In accordance with the present invention, the purity of a first gas in a binary mixture of that first gas and a known second gas may be continuously monitored and measured on a real time basis where the mixture is being circulated in a closed system by a fan. The method finds particular application for the continuous monitoring and measurement of hydrogen gas purity in a hydrogen/air mixture comprising a cooling gas circulated in the housing of a large electric generator.

In accordance with the method of the present invention, a first differential pressure across the fan is determined with the fan operating at a first speed and with said first gas at essentially 100% purity in the system. This first fan differential pressure provides a fan differential constant which is unique to the fan operating at the speed at which the constant is determined. To determine the purity of the first gas in any other mixture with a second gas, a second differential pressure across the fan is measured and the direct equality between the ratios of said first and second fan differential pressures and the densities of said first gas and the gas mixture (or the molecular weights of the first gas and the gas mixture) can be utilized to calculate the volume percent purity of the first gas directly. Differential pressure must be measured in consistent units of static, velocity, or total pressure. Appropriate adjustments can be made to correct the first gas purity calculation, if necessary, for variations in system pressure and temperature, in accordance with the ideal gas law. In addition, the known relationship between system pressure and fan speed, pursuant to the fan laws, may be utilized to correct the calculated first gas purity for differences in fan speed.

The first fan differential pressure at 100% purity of the first gas, also hereinafter referred to as the fan constant, may be measured directly or may be calculated on the basis of the foregoing ratios. In a preferred embodiment, the first fan differential pressure is determined by measuring the actual fan differential pressure with the system containing any mixture of said first and second gases, measuring the actual volume percent purity of the first gas in that mixture (as with a conventional thermal gas analyzer), and then calculating said first fan differential pressure in accordance with the same proportional relationships previously mentioned. If the fan constant represented by the first fan differential pressure is calculated in this manner, it is preferable to establish the constant at a standard pressure and temperature level. For example, the constant may be set at zero system gage pressure and a standard temperature representative of normal operating temperature levels. Then, when the second fan differential pressure is measured for the purpose of determining the purity of the first gas in any other mixture with the known second gas, measured system pressure and temperature at the second fan differential pressure may be used to easily correct the calculated purity in accordance with the ideal gas laws. The method disclosed herein may also be expanded to compensate for the actual presence of water vapor in the gas mixture, to provide a correction factor for thermal gas analyzer measurement of hydrogen purity, and to use corrected thermal gas analyzer purity to determine actual water vapor content in the mixture.

All of the measured variables are readily measurable in a typical hydrogen-cooled AC generator and the monitoring of hydrogen gas purity is readily adapted to microprocessor control.

DETAILED DESCRIPTION OF THE DRAWINGS

DETAILED DESCRIPTION OF THE PREFERRED EMBODIMENT

Figure 1:
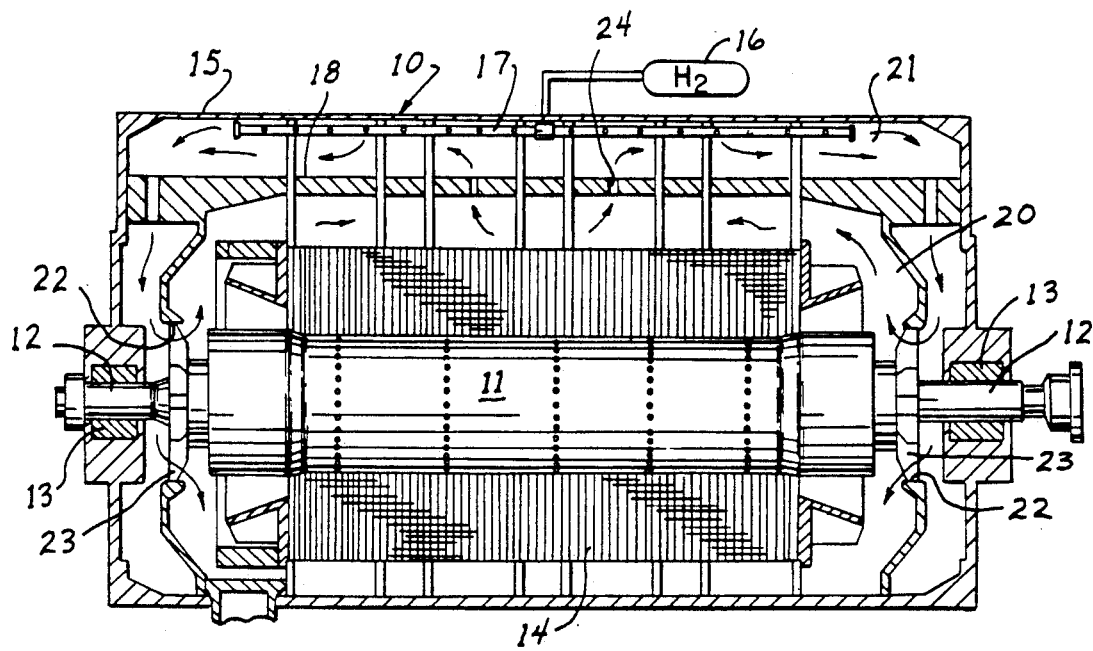
FIG. 1 is a vertical cross section through the axis of a hydrogen-cooled synchronous AC generator for which the method of the present invention is particularly adapted.

Referring first to FIG. 1, a typical large synchronous AC generator 10, includes a main shaft 12 rotatably mounting a rotor 11 by its opposite ends in a pair of main bearings 13. The stator 14 surrounds the rotor 11 and is mounted in a fixed position With respect thereto in an enclosing housing 15.

Hydrogen gas is supplied to the interior of the housing 15 from an external hydrogen supply 16 and is distributed within the housing by a hydrogen gas header 17. The hydrogen header 17 is separated from the rotor 11 and stator 14 by an interior cooling chamber wall 18 dividing the interior of the housing 15 into a cooling chamber 20 and a supply chamber 21. The opposite axial end walls of the cooling chamber wall 18 include circular openings which surround the main shaft 12 and within which are disposed a pair of shaft-mounted gas circulation fans 23. The fans 23 rotate with the main shaft and the generator rotor 11 to circulate hydrogen gas from the supply chamber 21 into and through the cooling chamber 20, to carry heat from the rotor and stator, and to return the gas to the supply chamber via outlet openings 24 in the outer radial walls of the cooling chamber 20. Passive heat transfer devices in the supply chamber 21 remove heat from the hydrogen gas which is recirculated in the closed system back through the cooling chamber 20.

The hydrogen gas is maintained at a very high purity in the range of 95% to 99+% subject to slight dilution by air which unavoidably seeps into the system. The high volume percent purity of hydrogen in the cooling gas mixture is desirable because of the very much greater thermal conductivity of hydrogen as compared to air and because at high hydrogen purity the mixture is nonexplosive and will not support combustion.

Increasing the hydrogen concentration by increasing the system pressure also enhances heat transfer and allows a generator to be operated at higher loads. Typically, a system pressure of 60 psi is maintained on a large synchronous AC generator operating at 3600 RPM and full load. Because of the importance of high hydrogen gas purity in the mixture to provide both effective cooling and a non-combustible mixture, hydrogen purity within the generator housing must be continuously monitored and maintained within the indicated safe range. Suitable alarm systems are typically provided so that hydrogen gas from the external supply 16 may be added whenever the hydrogen purity and/or the system pressure within the housing 15 drop below threshold levels. Hydrogen loss typically is a result of normal leakage through the seals and the absorption of hydrogen by lubricating oil.

Typical prior art hydrogen purity monitoring devices utilize the high thermal conductivity of hydrogen versus air as an indicator of hydrogen purity because the mixture of air or virtually any other gas with hydrogen will produce a substantially lower thermal conductivity than pure or high purity hydrogen gas. However, as indicated previously, thermal gas analyzers require a complex sampling and operating system, including a dryer to remove water vapor from the hydrogen/air mixture before sampling, and are typically very slow to react to changes in hydrogen purity.

It has long been known that differential fan pressure across the fans 23 is proportional to the density of the gas being circulated and, with an air/hydrogen mixture, differential fan pressure can be utilized as an indication of the purity of the hydrogen in the hydrogen/air mixture. Differential fan pressure is utilized to operate a manometer calibrated to show hydrogen purity directly. However, such a manometer is typically difficult to read and is used only as a backup to provide a rough independent check on the thermal gas analyzer.

Figure 2:
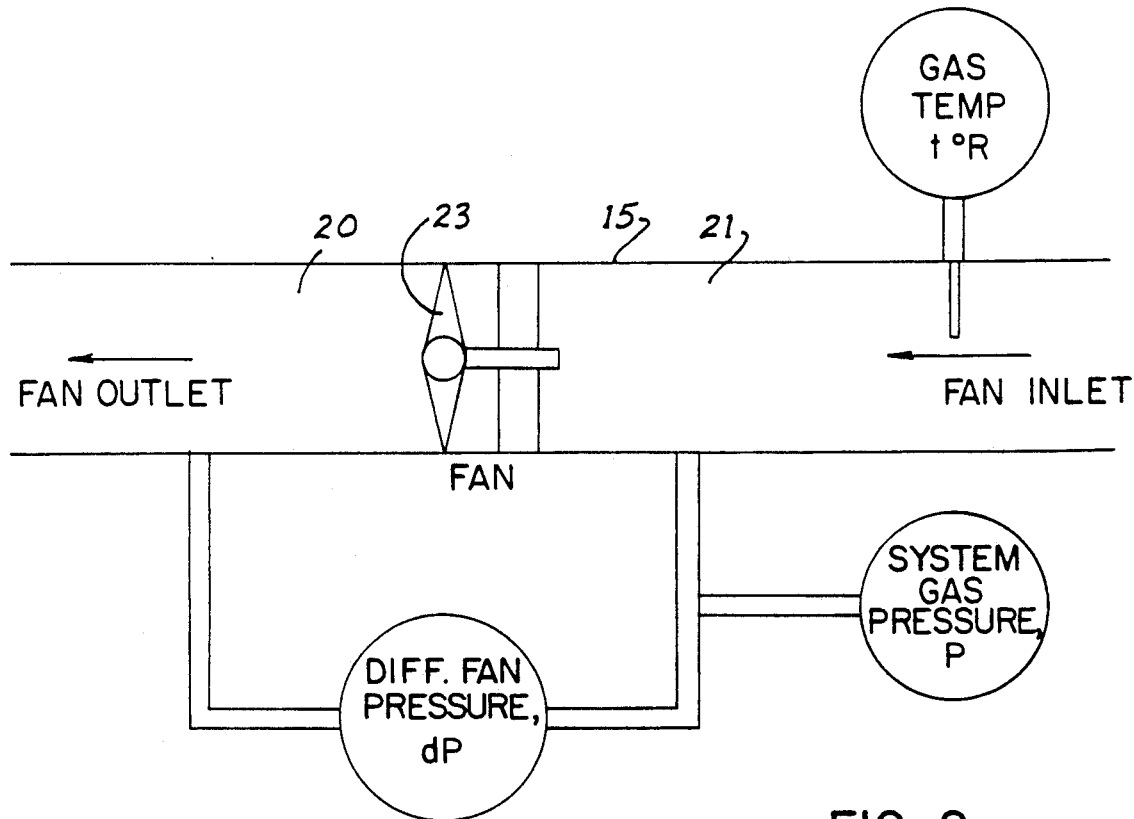
FIG. 2 is a schematic representation of a closed gas circulation system showing the various measured values used to calculate the purity of one of the gases in the circulating binary gas mixture.

A typical synchronous AC generator 10 may include a supplementary purity measuring fan or may be readily modified to provide for the measurement of differential pressure across the cooling gas circulating fans 23, system gas pressure within the housing (typically taken upstream of the fans in the supply chamber 21), and the temperature of the cooling gas within the housing (which may be taken at a place to provide a typical gas temperature or at several locations which may be arithmetically averaged). The method of the present invention is also dependent on fan speed, however, this is typically not a factor in the application of the method to a synchronous generator which operates at a constant carefully controlled speed. The various measured variables are shown schematically in FIG. 2.

The method of the present invention utilizes the various measured conditions within the generator housing, identified above, as well as a fan differential pressure factor which is constant for a given fan operating at a constant speed, and the proportional relationships between fan differential pressure and gas density (or molecular weight) to calculate the purity of hydrogen gas directly. The calculation can be made with the use of a computer or microprocessor such that continuous, real time monitoring of hydrogen purity is attainable.

The fundamental relationship upon which the method of the present invention is based may be expressed by the following equation:

$$\frac{dP_M}{dP_1} = \frac{D_M}{D_1} \quad (1)$$

Equation (1) expressed the known relationship based on conventional fan laws that, in a fan running at a constant speed, the ratio of the fan differential pressures for two different gases is equal to the ratio of their respective densities. In particular, the ratio of the fan differential pressure circulating a gas mixture, $dP_M$, and the fan differential pressure circulating a pure gas, $dP_1$, is equal to the ratio of the density of the binary gas mixture $D_M$ to the density of the pure gas $D_1$. In the example of the preferred embodiment of the present invention, the binary mixture is air and hydrogen and the gas of interest is hydrogen. Hydrogen and air both obey the ideal gas laws, as applied in the manner hereinafter described.

The fan differential pressure factor or fan constant, forming the basis of the gas purity calculation pursuant to the present invention, is a measure of the fan differential pressure at a known fan speed, pressure and temperature, utilizing a known gas at 100% purity. Because hydrogen is the gas of interest and its purity is monitored on a continuing basis, the fan differential pressure factor (fan constant) is determined for hydrogen gas at 100% purity in the system. The factor can be measured or calculated, as will be indicated hereinafter, and is used in conjunction with measured fan differential pressure, system pressure and temperature of any other mixture of air and hydrogen to determine the hydrogen purity in that mixture. Referring to equation (1) above, the fan differential pressure or fan constant, $dP_1$, may be determined by measuring the actual fan differential pressure directly with the system containing the gas of interest (hydrogen) at essentially 100% purity, calculated by measuring the foregoing variables utilizing a known gas purity, or using 100% dry air. For example, the purity of hydrogen in the system may be measured directly, as with a thermal gas analyzer. In any case, it is desirable for the sake of convenience to calculate or correct the fan constant to zero system pressure (atmospheric pressure) and a standard or typical operating temperature (e.g. 95° F.).

The purity of hydrogen gas (or other gas of interest in a mixture) to be determined in accordance with the method of the present invention, may be expressed in terms of the density of the gas mixture, $D_M$ in equation (1) by utilizing the relationship of the densities of the component gases in the mixture to the density of the mixture, pursuant to the following equation:

$$D_M = D_1(X) + D_2(1-X) \quad (2)$$

In equation (2), $D_M$ and $D_1$ are as indicated in equation (1), $D_2$ is the density of air (or other gas in the binary mixture), and X is the volume percent purity of hydrogen (or other gas of interest) expressed as a decimal fraction. The right hand side of equation (2) may be substituted for $D_M$ in equation (1), and the densities of hydrogen and air at any common temperature and pressure inserted therein for $D_1$ and $D_2$, respectively, as shown in the following equation:

$$\frac{dP_M}{dP_1} = \frac{[D_1(X) + D_2(1-X)]}{D_1} \quad (3)$$

However, in accordance with the universal gas laws, the density D of any ideal gas may be expressed in terms of its molecular weight w in accordance with the following equation:

$$D = \frac{wP}{RT} \quad (4)$$

In equation (4) P and T are the pressure and temperature at which density is determined and R is the universal gas constant. However, with respect to the density of the air/hydrogen mixture, $D_M$, as expressed in terms of the densities of its components, $D_1$ and $D_2$, the factor P/RT from equation (4) is a constant and, therefore, the right side of equation (3) may be expressed as follows:

$$\frac{dP_M}{dP_1} = \frac{[w_1(X) + w_2(1-X)]}{w_1}, \quad (5)$$

where $w_1$ and $w_2$ are the molecular weights of hydrogen and air, respectively. As indicated above, $dP_1$ is the fan constant or fan differential pressure factor for hydrogen gas (at a selected pressure and temperature) and $dP_M$ is the measured differential fan pressure in the system operating with the gas mixture and at which pressure it is desired to determine the purity, X, of the hydrogen gas.

Thus, $dP_1$ is measured or calculated in advance, $dP_M$ is measured at the time a purity determination is to be made, the molecular weights of hydrogen and air, $w_1$ and $w_2$, are known, and equation (5) can be solved for hydrogen purity, X. Because the differential pressures are affected by system temperature and pressure, appropriate corrections must be made for differences in temperature and pressure at which the respective differential pressures, $dP_1$ and $dP_M$ are calculated and/or measured, as shown in the following corrected version of equation (5):

$$\frac{dP_M\left(\frac{t_M}{P_M}\right)}{dP_1\left(\frac{t_1}{P_1}\right)} = \frac{w_1(X) + w_2(1-X)}{w_1} \quad (6)$$

or:

$$\frac{dP_M(t_M)(P_1)}{dP_1(t_1)(P_M)} = \frac{w_1(X) + w_2(1-X)}{w_1} \quad (7)$$

In equations (6) and (7), $t_1$ and $P_1$ are, respectively, the temperature in degrees R and system pressure at which the fan differential pressure factor was determined, which may conveniently be selected as, for example, 95° F. (555° R.) and atmospheric pressure (zero system pressure of 14.7 psia. $t_M$ and $P_M$ are, respectively, the actual temperature of the gas and the actual system gas pressure at the time the differential fan pressure, $dP_M$ is measured for the gas mixture the purity of the hydrogen component of which it is desired to determine. Thus, equation (6) or (7) is solved for the hydrogen purity, X, expressed as a decimal fraction. The system pressure $P_M$ (psig) comprises the measured gage pressure (psia), plus atmospheric pressure.

In the presently preferred method for determining the fan constant $dP_1$ which, as indicated above, is the fan differential pressure for the pure gas (i.e. hydrogen) at a given speed, system pressure and gas temperature. The following procedure is used. The actual differential fan pressure in a system circulating the binary gas mixture is measured, along with the gas temperature and system pressure. This provides the variables $dP_M$, $t_M$ and $P_M$. The molecular weights of the component gases $w_1$ (hydrogen) and $w_2$ (air) are known and the temperature and pressure, $t_1$ and $P_1$, may be selected at any desired level, as indicated. The purity of the hydrogen gas in that mixture is then measured (as with a thermal gas analyzer), and the purity value X inserted in the equation (6) or (7). The equation is then solved for $dP_1$, the fan constant or fan differential pressure factor. Once determined, this factor, along with the selected temperature and pressure $t_1$ and $P_1$ may be used to calculate the hydrogen gas purity at any other conditions of fan differential pressure, $dP_M$, temperature, $t_M$, and system pressure, $P_M$, so long as the fan speed remains constant.

Fan constant $dP_1$ could also be measured directly in a system operating at 100% purity of the first gas of interest. This measured differential fan pressure could be adjusted, if desired, to atmospheric pressure and a standard temperature, as previously indicated. Another method for determining $dP_1$ would utilize actual measured differential fan pressure with the other as of the mixture at 100% purity, and back-calculating $dP_1$ in accordance with the relationship set forth hereinabove.

In the application of the method of the present invention to calculating and monitoring hydrogen purity in the cooling gas circulated inside a large synchronous AC generator, certain unique factors exist which affect the accuracy needed in determining measured conditions and the detail needed in providing results which are accurate and meaningful. When the generator is operating at full load, the gas temperature rarely varies by more than about 5° F. Therefore, with the temperatures $t_1$ and $t_M$ expressed in degrees R, and a reference temperature $t_1$ selected at about the normal level of operating temperature, there is likely to be very little difference between the two temperatures. In other words, a 5° variation at 500° R. or higher only varies the ratio of $t_M$ to $t_1$ by 1% or less. Under certain circumstances, it may be possible to exclude temperature compensation from the calculation of hydrogen purity without a significant decrease in accuracy. In these systems, it is also desirable to maintain a fairly high and constant system pressure P, at a level for example of about 60 psig. Thus, if the actual system pressure is maintained fairly constant and the fan constant, $dP_1$, is calculated at that pressure, the system pressure ratio might also be omitted from the calculation of hydrogen purity without substantially affecting accuracy. However, because the actual variations in system pressure as a percentage of the base or reference pressure $P_1$ are typically much larger than corresponding differences in temperature, it is preferred to continuously monitor and measure system pressure and use it in the calculation of hydrogen purity. Also, since the speed of a generator must be maintained constant when on-line, there is typically no need to compensate for differences in speed between the speed at which the fan constant was determined and the speed at which the fan differential pressure is measured for hydrogen purity determination. However, it may be desirable in certain circumstances to be able to continue to monitor hydrogen purity as a generator is being brought on or taken off-line such that the speed may be constantly increasing or decreasing. In accordance with the fan laws, the system or differential fan pressure varies directly with the square of the fan speed. If the ratio of the fan speed at which the fan constant $dP_1$ was determined and the fan speed at which the differential fan pressure circulating the gas mixture for purity determination was measured is relatively small, i.e. less than 3, a correction factor may be applied to equation (6) or (7) to correct for speed variations, as follows:

$$\left( \frac{RPM_1}{RPM_M} \right)^2, \tag{8}$$

where $RPM_1$ is the speed at which the fan constant is determined and $RPM_M$ is the fan speed at which the hydrogen purity determination is made. The correction factor is applied by multiplying the measured fan differential pressure, $dP_M$, by the factor, e.g. the left hand side of equation (7).

A microprocessor may be appropriately programmed and connected to a generator to provide continuing real time calculations of hydrogen purity. Each of the measured conditions, fan differential pressure, system gas pressure and gas temperature can be continuously measured, converted to appropriate digital signals and supplied to a microprocessor for purity calculations as described hereinabove. Generator speed could also be continuously monitored and an appropriate speed signal provided to the microprocessor to calculate and apply the speed correction factor (8) should any variation in speed occur. It is also possible to utilize analog outputs of the various measured conditions to provide a direct reading analog output of hydrogen (or other gas) purity. However, digital processing is far simpler and is the presently preferred method.

The method of the present invention may also be used to determine the purity of one gas in a binary mixture of two known gases inside a housing where there is no internal gas circulating fan, as in the case of a gas storage vessel or pipeline. In that situation, a small fan could be placed in a duct system which is connected to the housing to draw gas out of it, circulate it through the fan, and return it to the housing through the other end of the duct. Differential pressure across the fan, as well as system gas pressure and temperature, could all be measured in the same manner shown in FIG. 2. The fan constant or fan differential pressure factor $dP_1$ could be determined in precisely the same way as indicated with respect to the generator application.

Described to this point, the method of the present invention when applied to the measurement of hydrogen purity in a generator has not considered the presence of moisture in the gas mixture. However, water vapor is inherently present in the hydrogen/air mixture and its presence is known to be potentially detrimental to certain internal generator components. Moisture in the gas mixture reduces the heat transfer efficiency and increases the power required to circulate the cooling gas mixture. In addition, however, the presence of moisture in the gas mixture and the failure to compensate for its presence may also result in inaccurate hydrogen purity measurements.

As mentioned above, the determination of hydrogen purity in a generator using a thermal gas analyzer requires that the gas sample be dried before measurement and, as a result, all moisture is removed from the sample. Thus, moisture as an impurity or additional component in the mixture is totally neglected. In the method of the present invention as thus far set forth, although no specific measurement of the moisture vapor fraction has been made, the measurements taken and utilized in calculating hydrogen purity utilize the actual mixed gas sample including water vapor. As a result, even without specifically accounting and correcting for moisture content, the basic method of the present invention treating the gas as a binary mixture still partially compensates for moisture to the extent that moisture is treated as a part of the air fraction. Nevertheless, full correction for moisture content in the gas would provide a more accurate determination of hydrogen purity.

Utilizing Dalton's law of partial pressures which states that the pressure exerted by a mixture of gases is equal to the sum of the pressures of each of its component gases, the relationship in a mixture of hydrogen, air and water vapor may be expressed as follows:

$$P_M = P_{H2} + P_A + P_{dp} \tag{9}$$

where,
$P_M$ = pressure of the mixture or actual system gas pressure as set forth in (6) and (7) above
$P_{H2}$ = pressure of the hydrogen gas
$P_A$ = pressure of the air
$P_{dp}$ = pressure of the water vapor at the dew point temperature.

The mole fraction of any component of the gas mixture, as a decimal fraction, may be expressed as follows:

$$X = \frac{P_{H2}}{P_M}, \quad X_A = \frac{P_A}{P_M}, \quad X_w = \frac{P_{dp}}{P_M}, \tag{10}$$

where X and $X_A$ and $X_W$ equal, respectively, the volume fractions (purities) of hydrogen, air and water vapor in the mixture, expressed as decimal fractions.

Rewriting equation (7) to include the water vapor fraction results in the following: where $w_3$ = molecular weight of water.

$$\frac{dP_M(t_M)(P_1)}{dP_1(t_1)(P_M)} = \frac{w_1 X + w_2(1 - X - X_w) + w_3(X_w)}{w_1} \tag{11}$$

Substituting for $X_W$ from the equation at (10):

$$\frac{dP_M(t_M)(P_1)}{dP_1(t_1)(P_M)} = \frac{w_1 X + w_2\left(1 - X - \dfrac{P_{dp}}{P_M}\right) + w_3\left(\dfrac{P_{dp}}{P_M}\right)}{w_1} \tag{12}$$

The vapor pressure at the dew point temperature may be determined by direct vapor pressure measurement, measuring the dew point temperature and selecting the corresponding vapor pressure from a steam table, or measuring the relative humidity and calculating the dew point temperature for use in a steam table. Equation (12) is then solved for the hydrogen purity, X, in essentially the same manner as equation (6) or (7), with appropriate corrections for temperature and pressure as previously described. The result is a hydrogen purity, expressed as a decimal fraction, fully corrected for moisture content.

The principles applied above in equations (9)–(12) to correct the calculated hydrogen purity for water vapor content may also be utilized to develop a correction factor for hydrogen purity measured by the use of a thermal gas analyzer. Furthermore, once hydrogen purity measured by a thermal gas analyzer is properly corrected to compensate for the actual presence of water vapor, the corrected hydrogen purity measurement may be combined with the method of the present invention to calculate actual moisture content in a mixture of hydrogen, air and water vapor in accordance with equation (11) or (12).

The measured hydrogen purity obtained from a thermal gas analyzer is based on a dried sample which contains no moisture. As a result, Dalton's law of partial pressures for the dried sample containing only hydrogen and air results in a simplification of equation (9), as follows:

$$P_M = P_{H2} + P_A \tag{13}$$

Dividing both sides of equation (13) by $P_M$ results in the following:

$$\frac{P_M}{P_M} = \frac{P_{H2}}{P_M} + \frac{P_A}{P_M} = 1 \tag{14}$$

Utilizing the equalities from (10), equation (14) may be rewritten and the hydrogen and air purities uncorrected for moisture may be expressed as follows:

$$X_{H2}(uncorrected) + X_A(uncorrected) = 1 \tag{15}$$

If the water vapor content is considered separately and the hydrogen and air fractions expressed in their corrected forms, equation (15) may be rewritten as follows:

$$X + X_A + X_w = 1 \tag{16}$$

where X, $X_A$ and $X_w$ are the true component gas fractions as used in equations (10)–(12) above.

Rewriting (16):

$$\frac{X + X_A}{1 - X_w} = 1 \tag{17}$$

Combining (15) and (17):

$$X_{H2}(uncorrected) + X_A(uncorrected) = \frac{X + X_A}{1 - X_w} \tag{18}$$

At 100% hydrogen (no air in the gas mixture), equation (18) becomes:

$$X_{H2}(uncorrected) = \frac{X}{1 - X_w} \tag{19}$$

Substituting $P_{dp}/P_M$ for $X_w$ from equation (10) and solving for the true hydrogen purity X, the measured and uncorrected hydrogen purity $X_{H2}$ may be corrected for $$X_{H2}\left(1 - \frac{P_{dp}}{P_M}\right) = X \qquad (20)$$

The dew point pressure, $P_{dp}$ may be measured or calculated as previously indicated, and the actual system gas pressure, $P_M$ may also be conveniently measured. Thus, the thermal gas analyzer measurement of hydrogen purity, uncorrected for moisture content, may be easily corrected and in all cases where moisture is present the corrected value will be lower than the measured purity.

In systems utilizing a thermal gas analyzer to determine hydrogen purity, that uncorrected measured hydrogen purity multiplied by the indicated correction factor may be substituted for the actual hydrogen purity, X, in either equation (11) or (12), which are then solved for the moisture content, $X_w$, or the dew point $P_{dp}$, with the latter being easily convertible back to the moisture content.

Various modes of carrying out the present invention are contemplated as being within the scope of the following claims particularly pointing out and distinctly claiming the subject matter which is regarded as the invention.

I claim:

1. A method for determining the purity of a known first gas in a mixture of the first gas, a second known gas, and a water vapor fraction, said mixture being circulated in a closed system by a fan, comprising the steps of:
   (1) determining a first fan differential pressure with the fan operating at a first speed and with said first gas at essentially 100% purity in the system;
   (2) measuring a second fan differential pressure with the fan operating at said first sped and with the gas mixture in the system;
   (3) utilizing the ratio of said first and second fan differential pressures to calculate the volume percent purity of said first gas in accordance with the equations:

$$\frac{dP_M}{dP_1} = \frac{W_M}{W_1};$$

and, $$W_M = W_1(X) + W_2\left(1 - X - \frac{P_{dp}}{P_M}\right) + W_3\left(\frac{P_{dp}}{P_M}\right),$$

where:
X = volume percent purity of said first gas as a decimal fraction
$dP_M$ = measured fan differential pressure with the gas mixture
$dP_1$ = fan differential pressure with the first gas
$w_M$ = molecular weight of the gas mixture
$w_1$ = molecular weight of the first gas
$w_2$ = molecular weight of the second gas
$w_3$ = molecular weight of water
$P_{dp}$ = vapor pressure of water vapor at the dew point temperature $P_M$ = measured pressure of the gas mixture in the system (4) correcting said first gas purity calculation, if necessary, for variations in system pressure and temperature.

2. The method as set forth in claim 1 wherein said first differential pressure is determined by measuring the actual fan differential pressure with the system containing said first gas at essentially 100% purity.

3. The method as set forth in claim 1 wherein said first differential pressure is determined by measuring the actual fan differential pressure with the system containing said second gas at essentially 100% purity, and calculating said first fan differential pressure in accordance with the equation:

$$\frac{dP_1}{dP_2} = \frac{w_1}{w_2},$$

where $dP_2$ = measured fan differential pressure with said second gas.

4. The method as set forth in claim 1 wherein said first fan differential pressure is determined by measuring the actual fan differential pressure with the system containing a mixture of said first and second gases, measuring the volume percent purity of said first gas in said mixture at said measured fan differential pressure, and calculating said first fan differential pressure in accordance with the equation set forth in step (3), where:
X = measured volume percent purity of said first gas as a decimal fraction.

5. The method as set forth in claim 4 including the additional steps of:
   calculating said first fan differential pressure at zero system pressure; and,
   adjusting said calculated volume percent purity for the difference between said measured system pressure and zero system pressure.

6. The method as set forth in claim 5 wherein said first fan differential pressure is calculated at a standard temperature and including the additional steps of:
   measuring the temperature of the gas mixture at said measured fan differential pressure; and,
   adjusting said calculated volume percent purity for the difference between the measured temperature and the standard temperature.

7. The method as set forth in claim 2, 3 or 4 wherein the closed system comprises an AC generator operating in a closed housing and wherein said first and second gases are hydrogen and air, respectively.

8. The method as set forth in claim 7 including the additional steps of:
   (1) continuously measuring said second fan differential pressure, system pressure, and gas mixture temperature;
   (2) generating digital signals representative of said pressures and temperature; and,
   (3) utilizing a programmed microprocessor to calculate said first gas purity from said digital signals on a real time basis.

9. The method as set forth in claim 7 including the additional steps of:
   (1) continuously measuring said second fan differential pressure, system pressure, and gas mixture temperature;
   (2) generating analog signals representative of said pressure and temperature;

(3) calculating said first gas purity from said analog signals; and,
(4) providing a direct analog reading of said first gas purity.

10. The method as set forth in claim 1 comprising the modified step of measuring said second fan differential pressure at a known second speed different from said first speed, and including the additional step of correcting said first gas purity for the difference in said first and second speeds.

11. The method as set forth in claim 10 wherein said first gas purity is corrected by multiplying said measured fan differential pressure by the factor:

$$\left(\frac{RPM_1}{RPM_M}\right)^2,$$

where $RPM_1$=first fan speed, and $RPM_M$=second fan speed.

12. A method for correcting the measured volume fraction of a first gas in a mixture of two known gases additionally containing water vapor in a closed system, said method comprising the steps of:
(1) obtaining a sample of said mixture containing water vapor from the system;
(2) drying the sample to remove the water vapor;
(3) measuring the volume fraction of the first gas in the dry sample;
(4) measuring the pressure $P_M$ of the gas mixture in the system;
(5) determining the dew point pressure $P_{dp}$ of the water vapor in the gas mixture; and
(6) correcting the measured volume fraction to obtain the true volume fraction of the first gas corrected for water vapor content in accordance with the equation:

$$X_c = X_U\left(1 - \frac{P_{dp}}{P_M}\right)$$

where
$X_C$=the true corrected volume fraction of the first gas and
$X_U$=the measured uncorrected volume fraction of the first gas.

13. The method as set forth in claim 12 wherein said step of measuring the volume fraction of said first gas comprises utilizing a thermal gas analyzer.

14. The method as set forth in claim 13 wherein said gas mixture comprises hydrogen and air.

15. A method for determining the water vapor fraction by volume in a mixture of two known gases containing water vapor, said mixture being circulated in a closed system by a fan, comprising the steps of:
(1) determining a first fan differential pressure with the fan operating at a first speed and with one of said known gases at essentially 100% purity in the system;
(2) measuring a second fan differential pressure with the fan operating at said first speed and with the gas mixture in the system;
(3) measuring volume fraction of said one gas from a sample of said gas mixture from which the water vapor has been removed;
(4) utilizing the ratio of said first and second fan differential pressures to calculate the volume fraction of water vapor in accordance with the equations:

$$X = X_u(1 - X_w)$$

and $$w_1\left(\frac{dP_M}{dP_1}\right) = w_1(X) + w_2(1 - X - X_w) + w_3(X_w).$$

where:
$X_w$=volume percent of water vapor in the mixture as a decimal fraction;
$X$=the actual volume percent of said one gas as a decimal fraction
$X_U$=the measured volume fraction of said one gas from step (3);
$dP_M$=measured fan differential pressure with the gas mixture;
$dP_1$=fan differential pressure with said one gas;
$w_1$=molecular weight of said one gas;
$w_2$=molecular weight of the other gas;
$w_3$=molecular weight of water;
(5) correcting said first gas purity calculation, if necessary, for variations in system pressure and temperature.

* * * * *